United States Patent
Ollila

(10) Patent No.: US 11,567,567 B2
(45) Date of Patent: Jan. 31, 2023

(54) ENCODERS, METHODS AND DISPLAY APPARATUSES INCORPORATING GAZE-DIRECTED COMPRESSION RATIOS

(71) Applicant: Varjo Technologies Oy, Helsinki (FI)

(72) Inventor: Mikko Ollila, Tampere (FI)

(73) Assignee: Varjo Technologies Oy, Helsinki (FI)

( * ) Notice: Subject to any disclaimer, the term of this patent is extended or adjusted under 35 U.S.C. 154(b) by 12 days.

(21) Appl. No.: 17/096,106

(22) Filed: Nov. 12, 2020

(65) Prior Publication Data

US 2022/0147140 A1    May 12, 2022

(51) Int. Cl.
*G06F 3/01* (2006.01)
*G02B 27/01* (2006.01)

(52) U.S. Cl.
CPC ......... *G06F 3/013* (2013.01); *G02B 27/0179* (2013.01); *G02B 2027/0187* (2013.01)

(58) Field of Classification Search
CPC ............... G06F 3/013; G02B 27/0179; G02B 2027/0187
See application file for complete search history.

(56) References Cited

U.S. PATENT DOCUMENTS

| 8,184,069 | B1 * | 5/2012 | Rhodes | G02B 27/017 348/115 |
| 2002/0141614 | A1 * | 10/2002 | Lin | H04N 19/17 375/E7.182 |
| 2018/0136720 | A1 * | 5/2018 | Spitzer | G06F 3/013 |
| 2020/0058152 | A1 * | 2/2020 | Zhang | G06T 15/005 |
| 2020/0167999 | A1 * | 5/2020 | Schmit | G06F 3/013 |

OTHER PUBLICATIONS

Bokani et al, "Predicting the Region of Interest for Dynamic Foveated Streaming", 2015 International Telecommunication Networks and Applications Conference,, pp. 137-142, XP032840065, DOI: 10.1109/ATNAC.2015.7366802, Nov. 18, 2015, 6 pages.

Cheng et al, "Gaze Location Prediction for Broadcast Football Video Using Bayesian Integration of Low Level Features and Top-Down Cues", IEEE International Conference on Image Processing, pp. 226-230, XP032965665, DOI: 10.1109/ICIP.2013.6738047, 6 pages.

Hwang et al, "Human Eye Interfaced Multiple Video Objects Coding", Visual Communications and Image Processing, XP030080660, Jul. 8, 2003, 12 pages.

(Continued)

*Primary Examiner* — Kwang-Su Yang
(74) *Attorney, Agent, or Firm* — Ziegler IP Law Group, LLC

(57) ABSTRACT

An encoder for encoding images. The encoder includes processor. The processor is configured to: receive, from display apparatus, information indicative of at least one of: head pose of user, gaze direction of user; identify gaze location in input image, based on the at least one of: head pose, gaze direction; divide input image into first input portion and second input portion, wherein first input portion includes and surrounds gaze location; and encode first input portion and second input portion at first compression ratio and at least one second compression ratio to generate first encoded portion and second encoded portion, respectively, wherein at least one second compression ratio is larger than first compression ratio.

20 Claims, 3 Drawing Sheets

(56) References Cited

OTHER PUBLICATIONS

Khan et al, "A Hybrid Scheme for Perceptual Object Window Design with Joint Scene Analysis and Eye-Gaze Tracking for Media Encoding based on Perceptual Attention", Visual Communication and Image Processing, XP030081399, Jan. 20, 2004, 12 pages.
Notification of Transmittal of The International Search Report and The Written Opinion of The International Searching Authority, or The Declaration, Application No. PCT/FI2021/050647, dated Dec. 13, 2021, 15 pages.
Vetro et al., "MPEG-4 Rate Control for Multiple Video Objects", IEEE Transactions on Circuits and Systems for Video Technology, vol. 9, No. 1, XP011014547, ISSN: 1051-8215, 14 pages.

* cited by examiner

ENCODERS, METHODS AND DISPLAY APPARATUSES INCORPORATING GAZE-DIRECTED COMPRESSION RATIOS

TECHNICAL FIELD

The present disclosure relates to encoders for encoding images. Moreover, the present disclosure also relates to methods for encoding images. Furthermore, the present disclosure also relates to display apparatuses.

BACKGROUND

An extended-reality (XR) device requires a sequence of XR images, to be able to present an XR environment to a user of the XR device. Typically, the sequence of XR images are obtained by the XR device from an image source (such as a computing device or a rendering server). The XR device and the image source are communicably coupled to each other via a data communication network.

Typically, image encoders are employed at the image source to compress the sequence of XR images prior to sending to the XR device. This compression is performed to manage data transmission requirements between the image source and the XR device, given the transmission resources of the data communication network. Then, at the XR device, the obtained sequence of XR images (that are in the compressed form) are decompressed and the decompressed sequence of XR images are displayed at light source(s) of the XR device.

However, conventional image encoders have certain limitations associated therewith. The image encoders typically employ compression techniques wherein an entirety of an XR image is compressed at a same compression ratio. Higher the compression ratio, lower is an amount of data to be transmitted over the data communication network. Consequently, lesser transmission resources are required for transmitting the highly-compressed XR image. However, the conventional image encoders sacrifice the image quality of the XR image to increase the compression ratio. Visual detail of the XR image is lost while compressing, thereby lowering the image quality of the XR image. The lowered image quality of the XR image is perceivable when the XR image (that is compressed at a high compression ratio) is decompressed and displayed at the light source(s). This adversely impacts realism and immersiveness of the user within the XR environment, which is undesirable for XR applications. The existing image encoders are unable to achieve a reasonable trade-off between reducing the amount of data to be transmitted over the data communication network and providing an acceptable level of image quality of the XR image.

Therefore, in light of the foregoing discussion, there exists a need to overcome the aforementioned drawbacks associated with conventional image encoders.

SUMMARY

The present disclosure seeks to provide an encoder for encoding images. The present disclosure also seeks to provide a method for encoding images. The present disclosure also seeks to provide a display apparatus. An aim of the present disclosure is to provide a solution that overcomes at least partially the problems encountered in prior art.

In one aspect, an embodiment of the present disclosure provides an encoder for encoding images, the encoder comprising a processor configured to:
  receive, from a display apparatus, information indicative of at least one of: a head pose of a user, a gaze direction of the user;
  identify a gaze location in an input image, based on the at least one of: the head pose of the user, the gaze direction of the user;
  divide the input image into a first input portion and a second input portion, wherein the first input portion includes and surrounds the gaze location; and
  encode the first input portion and the second input portion at a first compression ratio and at least one second compression ratio to generate a first encoded portion and a second encoded portion, respectively, wherein the at least one second compression ratio is larger than the first compression ratio.

In another aspect, an embodiment of the present disclosure provides a method for encoding images, the method comprising:
  receiving, from a display apparatus, information indicative of at least one of: a head pose of a user, a gaze direction of the user;
  identifying a gaze location in an input image, based on the at least one of: the head pose of the user, the gaze direction of the user;
  dividing the input image into a first input portion and a second input portion, wherein the first input portion includes and surrounds the gaze location; and
  encoding the first input portion and the second input portion at a first compression ratio and at least one second compression ratio to generate a first encoded portion and a second encoded portion, respectively, wherein the at least one second compression ratio is larger than the first compression ratio.

In yet another aspect, an embodiment of the present disclosure provides a display apparatus comprising at least one light source and a processor configured to:
  send, to an encoder, information indicative of at least one of: a head pose of a user, a gaze direction of the user;
  receive, from the encoder, a first encoded portion, a second encoded portion and information indicative of relative positions of a first input portion and a second input portion of an input image, the input image being divided at the encoder into the first input portion and the second input portion based on the at least one of: the head pose of the user, the gaze direction of the user, the first encoded portion and the second encoded portion being generated at the encoder by encoding the first input portion and the second input portion at a first compression ratio and at least one second compression ratio, respectively, the at least one second compression ratio being larger than the first compression ratio;
  decode the first encoded portion and the second encoded portion to generate a first decoded portion and a second decoded portion, respectively;
  assemble the first decoded portion and the second decoded portion, based on the relative positions of the first input portion and the second input portion, to generate an output image; and
  display the output image via the at least one light source.

Embodiments of the present disclosure substantially eliminate or at least partially address the aforementioned problems in the prior art, and enable gaze-directed compression of input images using different compression ratios in a manner that quality of gaze-contingent portions of the input images is well preserved during encoding, and data savings for transmission are also achieved.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those skilled in the art will understand that the drawings are not to scale. Wherever possible, like elements have been indicated by identical numbers.

Embodiments of the present disclosure will now be described, by way of example only, with reference to the following diagrams wherein.

Figure 1:
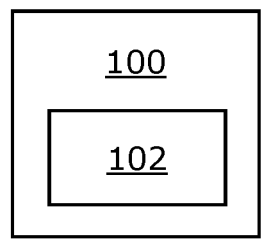
FIG. 1 illustrates an architecture of an encoder for encoding images, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

In one aspect, an embodiment of the present disclosure provides an encoder for encoding images, the encoder comprising a processor configured to:
receive, from a display apparatus, information indicative of at least one of: a head pose of a user, a gaze direction of the user;
identify a gaze location in an input image, based on the at least one of: the head pose of the user, the gaze direction of the user;
divide the input image into a first input portion and a second input portion, wherein the first input portion includes and surrounds the gaze location; and
encode the first input portion and the second input portion at a first compression ratio and at least one second compression ratio to generate a first encoded portion and a second encoded portion, respectively, wherein the at least one second compression ratio is larger than the first compression ratio.

In another aspect, an embodiment of the present disclosure provides a method for encoding images, the method comprising:
receiving, from a display apparatus, information indicative of at least one of: a head pose of a user, a gaze direction of the user;
identifying a gaze location in an input image, based on the at least one of: the head pose of the user, the gaze direction of the user;
dividing the input image into a first input portion and a second input portion, wherein the first input portion includes and surrounds the gaze location; and
encoding the first input portion and the second input portion at a first compression ratio and at least one second compression ratio to generate a first encoded portion and a second encoded portion, respectively, wherein the at least one second compression ratio is larger than the first compression ratio.

In yet another aspect, an embodiment of the present disclosure provides a display apparatus comprising at least one light source and a processor configured to:
send, to an encoder, information indicative of at least one of: a head pose of a user, a gaze direction of the user;
receive, from the encoder, a first encoded portion, a second encoded portion and information indicative of relative positions of a first input portion and a second input portion of an input image, the input image being divided at the encoder into the first input portion and the second input portion based on the at least one of: the head pose of the user, the gaze direction of the user, the first encoded portion and the second encoded portion being generated at the encoder by encoding the first input portion and the second input portion at a first compression ratio and at least one second compression ratio, respectively, the at least one second compression ratio being larger than the first compression ratio;
decode the first encoded portion and the second encoded portion to generate a first decoded portion and a second decoded portion, respectively;
assemble the first decoded portion and the second decoded portion, based on the relative positions of the first input portion and the second input portion, to generate an output image; and
display the output image via the at least one light source.

The present disclosure provides the aforesaid encoder which provides a reasonable trade-off between reducing the amount of data to be transmitted between the encoder and the display apparatus and providing an acceptable level of image quality of the output image. The encoder effectively utilizes at least one of: the head pose of the user, the gaze direction of the user, to divide the input image into multiple input portions, and employs different compression ratios for different input portions in a manner that an amount of compression is increased and image quality is decreased for input portions that lie away from the gaze location while an amount of compression is decreased and image quality is increased for input portions that correspond to the gaze location. In particular, the first input portion which corresponds to the gaze location is encoded at the first compression ratio which is smaller than the at least one second compression ratio employed for encoding the second input portion that is away from the gaze location. In this way, image quality is well-preserved for the first input portion while encoding, so that its corresponding portion in the output image is perceived with high realism and immersiveness by the user; and image quality is relatively lowered for the second input portion while encoding, so that data savings for transmission can be made efficiently.

Throughout the present disclosure, the term "image" refers to visual content, which encompasses not only data colour information represented in the image, but also other attributes associated with the image (for example, such as depth information, transparency information, and the like). It will be appreciated that the image can have a field of view from 40, 50, 60, 70, 80, 90, 100, 110, 120, 130, 140, 150, 160, 170, 180, 190, 200 or 210 degrees up to 50, 60, 70, 80, 90, 100, 110, 120, 130, 140, 150, 160, 170, 180, 190, 200, 210 or 220 degrees. Pursuant to embodiments of the present disclosure, the aforesaid encoder and the aforesaid method are suitable for encoding images having a wide variety of field of views.

Throughout the present disclosure, the term "encode?" refers to specialized equipment that, in operation, encodes images. The processor of the encoder executes the method for encoding images. The encoder encodes the input image to yield the first encoded portion and the second encoded portion (hereinafter collectively referred to as "encoded portions"). These encoded portions require lesser storage and transmission resources as compared to the input image. When the encoded portions are communicated to the display apparatus, the encoded portions are transmitted from the encoder to the display apparatus in a bandwidth-efficient manner.

Moreover, the term "display apparatus" refers to specialized equipment that is configured to present an extended-reality (XR) environment to the user when the display apparatus in operation is worn by the user on his/her head. In such an instance, the display apparatus acts as a device (for example, such as an XR headset, a pair of XR glasses, and the like) that is operable to present the XR environment to the user. Commonly, the "display apparatus" is referred to as "head-mounted display apparatus", for the sake of convenience only. The term "extended-reality" encompasses virtual reality (VR), augmented reality (AR), mixed reality (MR), and the like.

The display apparatus implements a corresponding decoder for the encoder. The encoded portions are decoded at the display apparatus to generate the first decoded portion and the second decoded portion (hereinafter collectively referred to as "decoded portions"). Such decoding is an inverse process of encoding. Components of the display apparatus are described later in detail.

The encoder is implemented in a computing device or a rendering server that is communicably coupled to the display apparatus. The computing device or the rendering server could be understood to be an image source of a sequence of input images. The computing device or the rendering server is configured to execute a rendering application. The rendering application, when executed, performs image rendering operations to generate the input image. These image rendering operations are optionally performed for XR applications, to generate XR input images. The computing device or the rendering server is coupled to the display apparatus either directly, or via a data communication network. The data communication network may be wired, wireless or any combination thereof. Examples of the computing device include, but are not limited to, a desktop computer, a laptop computer, a tablet computer, a workstation, and an XR console.

It will be appreciated that a required resolution for output images to be displayed at the display apparatus and a refresh rate of the at least one image source of the display apparatus is typically quite high. Therefore, compression is performed at the time of encoding by the encoder, to reduce a required bitrate for transferring data from the computing device or the rendering server to the display apparatus.

Throughout the present disclosure, the term "input image" refers to an image that is to be encoded. Optionally, the input image is an XR image. In such a case, the XR image represents an entirety of a scene in the XR environment or a portion of a scene in the XR environment. Separate input images are generated for each eye of the user. Optionally, the rendering application generates the input image. The input image may be generated by the rendering application entirely using computer graphics (for example, for VR environments), or may be generated by the rendering to application by adding computer graphics to an image of a given real-world environment (for example, for AR environments and MR environments). Optionally, the image of the given real-world environment is obtained by the computer or the rendering server from at least one camera of the display apparatus.

In some implementations, the input image has a uniform spatial resolution in its entirety. In other words, different input portions of the input image have same spatial resolution. In other implementations, the input image has a variable spatial resolution. In other words, different input portions of the input image have different spatial resolution. Optionally, a spatial resolution of the first input portion is greater than a spatial resolution of the second input portion. Herein, the term "spatial resolution" of a given region of a given image refers to a number of pixels per degree (also referred to as points per degree (PPD)) in the given region.

Optionally, the information indicative of the head pose of the user comprises head-tracking data, wherein the head-tracking data is indicative of a position and an orientation of the user's head in a three-dimensional coordinate space. The three-dimensional coordinate space could be a global coordinate space of the scene (of the XR environment), a local coordinate space of a given real-world environment where the user is present, or similar. It will be appreciated that the head pose of the user corresponds to a pose of the display apparatus, since the user wears the display apparatus on his/her head while using it. Therefore, optionally, the head-tracking data is indicative of a position and an orientation of the display apparatus in the three-dimensional coordinate space. The head pose of the user typically keeps changing as the user uses the display apparatus.

Optionally, the information indicative of the gaze direction of the user comprises a gaze vector that is indicative of the gaze direction of the user. The gaze vector extends from a given eye of the user to a location in a scene (of the XR environment) at which the given eye is gazing. It will be appreciated that different gaze vectors are received (by the processor of the encoder) for different eyes of the user, as each eye gazes at the location in the scene from a different angle.

Optionally, the processor of the encoder processes the information indicative of at least one of: the head pose of the user, the gaze direction of the user, to identify the gaze location in the input image. Throughout the present disclosure, the term "gaze location" refers to a location in the input image that corresponds to at least one of: the head pose of the user, the gaze direction of the user. In case of gaze-based compression, the gaze location can be a point that is identified based on the gaze direction of the user. In case of head-pose-based compression, the gaze location can be a point that is identified based on a line of vision of the user at infinity in a given head pose. Notably, the user is not shown the input image, but is instead shown the output image. At least one of: the head pose of the user, the gaze direction of the user, that is determined whilst the user views a given output image is used for determining a gaze location in a next input image corresponding to a next output image.

Optionally, the gaze location in the input image is identified by mapping the gaze direction of the user to a corresponding location in the input image. Optionally, in this regard, the gaze vector is mapped to the corresponding location in the input image. Optionally, the gaze location in the input image is identified by mapping the line of vision of the user at infinity in the given head pose to a corresponding location in the input image.

It will be appreciated that the gaze location in the input image may be anywhere in the input image. In an example, the gaze location may lie at a centre of the input image. In another example, the gaze location may lie at a point in a top-right portion of the input image.

Optionally, the input image is divided in a manner that the first input portion includes and surrounds the gaze location, whereas the second input portion corresponds to a remaining portion of the input image. Optionally, the second input portion surrounds the first input portion. The division of the input image is performed dynamically, according to the gaze location. According to known properties of the visual system of the user's eyes, the gaze location and a portion of the input image that immediately surrounds the gaze location would be resolved to a much greater degree of visual detail by the user's eyes, as compared to the remaining portion of the input image. This dynamic manner of dividing the input image according to a current head pose and/or a current gaze direction (and specifically, a current gaze location) of the user emulates a manner in which users generally focus within their field of view. By such division of the input image, there is facilitated active foveation-based encoding of the input image at the encoder.

Optionally, when dividing the input image, a shape of the first input portion is one of: a polygon (for example, a rectangle, a hexagon, and the like), a circle, an ellipse, a freeform shape.

In an example, the input image may have a size equal to 28*28 pixels and the gaze location may lie at a centre of the input image. In such a case, the input image may be divided into the first input portion having a size equal to 8*8 pixels that includes and surrounds the centre of the input image, and the second input portion which is the remaining portion of the input image. Therefore, the first input portion (having a square shape) includes 64 pixels, whereas the second input portion includes 720 pixels.

It will be appreciated that the input image is divided into at least two parts, which are to be compressed differently using different compression ratios during encoding. For example, the input portion may be divided into the first input portion, the second input portion, a third input portion, and so on.

Throughout the present disclosure, the term "compression ratio" refers to a measure of relative reduction in size of data that is obtained by applying an encoding algorithm to the data. A given compression ratio is expressed as a ratio of a data size of a given input portion to a data size of a given encoded portion, wherein the given encoded portion is generated upon encoding the given input portion. It will be appreciated that a data size of a given area of an image is represented by a number of bits required to store the given area of the image (also referred to as bits per area), wherein the given area could correspond to a single pixel or multiple pixels. As an example, the given compression ratio being equal to two means that a number of bits required to store the given input portion is twice of a number of bits required to store the given encoded portion. In other words, the data size of the given encoded portion is half of the data size of the given input portion.

It will be appreciated that employing different compression ratios for different input portions of the input image facilitates in improving image quality of the output image in requisite regions, whilst also enabling efficient reduction of data to be transferred between the encoder and the display apparatus. As the at least one second compression ratio is larger than the first compression ratio, the second input portion (which lies outside a region of interest of the user's gaze) is compressed to a larger extent than the first input portion (which is the region of interest of the user's gaze). In this way, the encoder incorporates gaze-directed compression. Notably, more visual detail is preserved at the time of encoding for the first input portion than for the second input portion, as the first input portion corresponds to the user's gaze. As a result, the output image would be generated in a manner that the first decoded portion (corresponding to the first input portion) has a higher quality as compared to the second decoded portion (corresponding to the second input portion). Since the first decoded portion corresponds to the gaze location of the user, it is desirable to present the first decoded portion at a high quality. However, since the second decoded portion does not correspond to the gaze location of the user, the second decoded portion may be shown at a relatively lower, but acceptable quality, to the user. Such variation of quality in the output image emulates the manner in which the users generally focus within their field of view, whilst also supporting efficient reduction of data to be transferred between the encoder and the display apparatus.

In some implementations, a single compression ratio is employed for encoding the entirety of the second input portion. In other implementations, a plurality of compression ratios is employed for encoding a plurality of parts of the second input portion. In such a case, different parts of the second input portion are compressed to different extents, depending on their corresponding compression ratio.

Optionally, the first compression ratio is smaller than a predefined number, and the at least one second compression ratio is larger than the predefined number. Optionally, the predefined number is selected from the group consisting of 1, 2, 3, and 4. Alternatively, the predefined number can have any other intermediate value, for example, 1.25, 2.7, and so on. The first compression ratio being smaller than the predefined number facilitates near-lossless encoding of the first input portion (which corresponds to the gaze location). This beneficially enables the first decoded portion to be generated in a manner that the first decoded portion appears naturally similar to the first input portion and has a high quality. Moreover, the at least one second compression ratio being larger than the predefined number enables efficient data compression of the second input portion (which does not correspond to the gaze location). The second encoded portion thus generated has a data size that is considerably smaller than the data size of the second input portion, and therefore the second encoded portion can be efficiently transmitted to the display apparatus as the required bitrate for transferring data gets reduced. Such values of the first compression ratio and the at least one second compression ratio enable in providing a rich viewing experience to the user by utilizing low compression for the gaze-contingent first input portion whilst efficiently reducing an amount of data to be transferred by utilizing high compression for the second input portion.

Optionally, the predefined number is selected based on an image format of the input image. As an example, the predefined number may be selected to be equal to four for Joint Photographic Experts Group (JPEG) image format or to be equal to two or three for Display Stream Compression (DSC) and texture compensations.

Optionally, the at least one second compression ratio is larger than twice the first compression ratio. In other words, a number of bits employed for encoding a given number of pixels in the first input portion is greater than twice the number of bits employed for encoding the given number of pixels in the second input portion. As a result, the quality of the first decoded portion is much better than the quality of the second decoded portion, which enables the display apparatus to emulate foveation properties of human visual system in the output image. In an example, 24 bits may be employed for encoding four pixels in the first input portion, whereas 8 bits may be employed for encoding four pixels in the second input portion.

Optionally, the first compression ratio is equal to one, and the at least one second compression ratio is larger than one. In such a case, the first input portion is encoded in a lossless manner while the second input portion is encoded in a lossy manner. In other words, the first input portion is not compressed, and only the second input portion is compressed.

Optionally, when encoding, the processor is configured to employ at least one first encoding algorithm and at least one second encoding algorithm to encode the first input portion and the second input portion, respectively. The at least one first encoding algorithm and the at least one second encoding algorithm are selected according to required values of the first compression ratio and the at least one second compression ratio, and available processing resources of the processor. It will be appreciated that the at least one first encoding algorithm and the at least one second encoding algorithm are single image frame compression techniques (for example, such as Joint Photographic Experts Group (JPEG), Portable Network Graphics (PNG), and the like), which enable in avoiding delays that are typically incurred with gaze movement predictions which happen in video streaming compression techniques. The at least one first encoding algorithm and the at least one second encoding algorithm may be selected from amongst encoding algorithms well-known in the art.

Optionally, the at least one first encoding algorithm comprises a plurality of first encoding algorithms that are employed to encode the first input portion in a sequential manner. Optionally, the at least one second encoding algorithm comprises a plurality of second encoding algorithms that are employed to encode the second input portion in a sequential manner.

In an example, a JPEG2000 encoding algorithm may be employed to encode the first input portion, whereas a JPEG-LS encoding algorithm may be employed to encode the second input portion. The JPEG-LS encoding algorithm is line based, is simpler than the JPEG2000 encoding algorithm, and requires few processing resources for its implementation.

In another example, the first input portion may be encoded by employing a texture encoding algorithm for texture compression, whereas the second input portion may be encoded by employing a plurality of second encoding algorithms. For example, the second input portion may be encoded by employing a texture encoding algorithm for texture compression and a JPEG encoding algorithm. The texture encoding algorithm may be a texture block compression algorithm (such as an S3 Texture Compression (S3TC) algorithm, Ericsson Texture Compression (ETC), PowerVR Texture Compression (PVRTC), Adaptive Scalable Texture Compression (ASTC), and the like) that divides an image representing texture in the input image into blocks, and compresses these blocks individually.

Optionally, the processor is configured to send, to the display apparatus, the first encoded portion, the second encoded portion, information indicative of relative positions of the first input portion and the second input portion. The information indicative of relative positions of the first input portion and the second input portion is sent along with the first encoded portion and the second encoded portion, to enable the display apparatus in correctly assembling the first decoded portion and the second decoded portion when generating the output image. Without said information, this assembling operation would be executed erroneously, which is undesirable. The relative positions of the first input portion and the second input portion (namely, how the first input portion and the second input portion are positioned with respect to each other in the input image) change dynamically according to the user's gaze. Therefore, said information is sent along with encoded portions of each input image that is sent to the display apparatus.

Optionally, the first encoded portion and the second encoded portion are in form of images. Optionally, the first encoded portion and the second encoded portion are sent together as one composite image.

Optionally, the processor is configured to send, to the display apparatus, information indicative of relative sizes of the first input portion and the second input portion. The relative sizes of the first input portion and the second input portion of the input image may, for example, be expressed as a ratio of a size of the first input portion and a size of the second input portion of the input image. A size of a given area of an image is, for example, represented as a number of pixels in the given area. As an example, the input image may have a size of 784 pixels (i.e. 28*28 pixels), wherein the first input portion has a size of 64 pixels (i.e. 8*8 pixels) and the second input portion has a size of 720 pixels. In such an example, the relative sizes of the first input portion and the second input portion of the input image may be 64:720, which is equal to 4:45.

In some implementations, the information indicative of relative sizes of the first input portion and the second input portion is sent, for each input image, to the display apparatus. These implementations pertain to embodiments wherein different input images are divided in a different manner from each other. In other implementations, the information indicative of relative sizes of the first input portion and the second input portion is sent only once to the display apparatus or is known to the display apparatus a priori. These implementations pertain to embodiments wherein different input images are divided in a similar manner.

It will be appreciated that the information indicative of relative sizes of the first input portion and the second input portion is required by the display apparatus, as said information is required when generating the first and second decoded portions by decoding the encoded portions. Notably, a size of the output image need not be the same as the size of the input image. Irrespective of the sizes of the output image and the input image, relative sizes of the first decoded portion and the second decoded portion are required to be equal or nearly-equal to the relative sizes of the first input portion and the second input portion. This enables in maintaining a consistent relative proportion of different portions of the visual content in the input image and the output image. Moreover, when decoding the encoded portions, spatial resolutions of the first input portion and the second input portion are required to be maintained for the first decoded portion and the second decoded portion, respectively.

Optionally, an angular width of the first input portion lies in a range of 5 degrees to 60 degrees. For example, the angular width of the first input portion may be from 5, 10, 15, 20, 25, 30, 35, 40, 45, 50, or 55 degrees up to 10, 15, 20, 25, 30, 35, 40, 45, 50, 55, or 60 degrees. It will be appreciated that the angular width of the first input portion could optionally be greater than 60 degrees.

Optionally, an angular width of the second input portion lies in a range of 40 degrees to 220 degrees. For example, the angular width of the second input portion may be from 40, 50, 60, 70, 80, 90, 100, 110, 120, 130, 140, 150, 160, 170, 180, 190, 200 or 210 degrees up to 50, 60, 70, 80, 90, 100, 110, 120, 130, 140, 150, 160, 170, 180, 190, 200, 210 or 220 degrees. Herein, the term "angular width" refers to an angular width of a given portion of an image with respect to the perspective of the user's eye, namely with respect to a centre of the user's gaze.

It will be appreciated that the angular widths of the first input portion and the second input portion will vary depending on a field of view (FOV) of the input image. As an example, if the input image is a regular two-dimensional (2D) image having an FOV smaller than 180 degrees, the angular width of the first input portion could be 30 degrees.

Optionally, the processor is configured to divide the second input portion into a plurality of input rings that are concentric with the first input portion, the first input portion and the plurality of input rings being shaped as a simple closed curve, wherein the first input portion and the plurality of input rings are centered at the gaze location in the input image, wherein, when encoding, the processor is configured to encode the plurality of input rings at different compression ratios into the second encoded portion, wherein a compression ratio employed to encode a given input ring is smaller than a compression ratio employed to encode another input ring that is larger than the given input ring.

Herein, the term "simple closed curve" refers to a connected curve that does not cross itself and ends at the same point where it begins. Examples of a given simple closed curve include, but are not limited to, polygons, circles, ellipses, rounded polygons, and freeform closed curves. Notably, despite use of the word "curve" in its name, a simple closed curve is not necessarily curved in shape. It will be appreciated that the given simple closed curve is made up of line segments only, curved lines only, or a combination of line segments and curved lines. When the given simple closed curve is made up of line segments only, the given simple closed curve is a polygon (for example, such as a square, a rectangle, a hexagon, an octagon, and the like). When the given simple closed curve is made up of curved lines only, the given simple closed curve has a curved shape (for example, such as a circle, an ellipse, and the like).

Optionally, sizes of the plurality of input rings increase on going from the centre of the plurality of input rings towards a periphery of the input image. Therefore, employing different compression ratios for different input rings provides a technical effect of intelligently compressing the second input portion of the input image in a manner that an extent of compression increases on going away from the gaze location of the user towards the periphery of the input image. In this way, the second input portion is encoded at a varying data size that emulates a manner in which visual detail is resolved by the user's eyes. An innermost input ring that is adjacent to the first input portion is closest to the gaze location and is therefore compressed the least to preserve its quality, whereas an outermost input ring that is farthest from the gaze location is compressed the most, the extent of compression increasing in a step-wise manner on going away from the innermost input ring to the outermost input ring.

As an example, the plurality of input rings may comprise 4 input rings a1, a2, a3 and a4, wherein said input rings a1-a4 are arranged sequentially such that the input ring a1 is closest to the gaze location and the input ring a4 is farthest from the gaze location. Four different second compression ratios employed for the input rings a1, a2, a3 and a4 may be 4:1, 16:1, 36:1 and 64:1, respectively.

Optionally, different input rings among the plurality of input rings have different spatial resolutions. Moreover, optionally, spatial resolutions of the plurality of input rings decrease on going from the centre of the plurality of input rings towards a periphery of the input image. Such a decrease in the spatial resolutions may be linear, non-linear, or step-wise.

In an embodiment, the processor is configured to:
divide the second input portion into the plurality of input rings based on a function of a distance of a given input ring from the gaze location in the input image, wherein thicknesses of the plurality of input rings increase on going from the gaze location towards a periphery of the input image according to said function; and
send, to the display apparatus, information indicative of said function.

Herein, the "distance" of the given input ring from the gaze location could be measured as an angular distance (namely, an angular separation) or as a number of pixels between the given input ring and the gaze location. In an embodiment, the distance of the given input ring from the gaze location is expressed as the angular distance, wherein the angular distance is expressed in terms of degrees. In another embodiment, the distance of the given input ring from gaze location is expressed as a number of pixels between the gaze location and a middle of the given input ring. The "middle of the given input ring" is a midpoint of a shortest line connecting inner and outer edges of the given input ring.

Optionally, the function of the distance of the given input ring from the gaze location in the input image is one of: a piecewise linear curve, a non-linear curve or a step-gradient curve. This function is defined such that an input ring that is closest to the gaze location has minimum thickness, whereas an input ring that is farthest from the gaze location has maximum thickness. Optionally, the function of the distance of the given input ring from the gaze location in the input image is defined by a Pixels Per Degree (PPD) curve. The PPD curve defines an angular resolution (namely, pixels per degree) within the input image.

Throughout the present disclosure, the "thickness" of the given input ring refers to a distance between a first point on an outer edge of the given input ring and a second point on an inner edge of the given input ring, the first point and the second point lying along a normal extending between the outer edge and the inner edge. Referring to the previous example, distances of (middle of) the input rings a1, a2, a3 and a4 from the gaze location may be 5 pixels, 8 pixels, 14 pixels, and 26 pixels, respectively. Therefore, the thicknesses of the input rings a1, a2, a3 and a4 may be 2 pixels, 4 pixels, 8 pixels and 16 pixels, respectively.

Optionally, the information indicative of the function of the distance of the given input ring from the gaze location in the input image is:
  sent only once to the display apparatus, provided that all input images of the sequence of input images are encoded in a similar manner;
  communicated repeatedly to the display apparatus, according to a rate at which input images are encoded; or
  pre-known to the display apparatus.

It will be appreciated that the information indicative of the function of the distance of the given input ring from the gaze location in the input image is sent from the encoder to the display apparatus for subsequent use at the display apparatus whilst decoding the second encoded portion. Said function, when analysed along with thicknesses of the plurality of input rings and the at least one second compression ratio, enables the display apparatus to determine at least one required decompression ratio for decoding the second encoded portion.

In another embodiment, the processor is configured to divide the second input portion into the plurality of input rings in a manner that the plurality of input rings have a same thickness.

Optionally, the second input portion is encoded by packing the plurality of input rings into the second encoded portion, the second encoded portion having a plurality of rows, a given input ring being packed into a corresponding row of the second encoded portion. Herein, the term "packing" refers to an image processing technique in which the plurality of input rings of the input image are compressed and rearranged into the second encoded portion in a manner that one input ring is packed into one row of the second encoded portion.

In some implementations, the plurality of rows have a same height. These implementations optionally correspond to the embodiments where thicknesses of the plurality of input rings are variable. In other implementations, heights of the plurality of rows depend on the function of the distance of a corresponding input ring from the gaze location in the input image. In this regard, the heights of the plurality of rows decrease as the distance of their corresponding input ring from the gaze location increases. These implementations optionally correspond to the embodiments where the plurality of input rings have the same thickness.

The present disclosure also relates to the method as described above. Various embodiments and variants disclosed above apply mutatis mutandis to the method.

Optionally, the method further comprises sending, to the display apparatus, the first encoded portion, the second encoded portion, information indicative of relative positions of the first input portion and the second input portion. Moreover, optionally, the method further comprises sending, to the display apparatus, information indicative of relative sizes of the first input portion and the second input portion.

Optionally, in the method, an angular width of the first input portion lies in a range of 5 degrees to 60 degrees.

Optionally, in the method, the first compression ratio is smaller than a predefined number, and the at least one second compression ratio is larger than the predefined number.

Optionally, in the method, the at least one second compression ratio is larger than twice the first compression ratio.

Optionally, in the method, the first input portion and the second input portion are encoded by employing at least one first encoding algorithm and at least one second encoding algorithm, respectively.

Optionally, the method further comprises dividing the second input portion into a plurality of input rings that are concentric with the first input portion, the first input portion and the plurality of input rings being shaped as a simple closed curve, wherein the first input portion and the plurality of input rings are centered at the gaze location in the input image,
wherein the step of encoding comprises encoding the plurality of input rings at different compression ratios into the second encoded portion, wherein a compression ratio employed to encode a given input ring is smaller than a compression ratio employed to encode another input ring that is larger than the given input ring.

Optionally, in the method, the step of dividing the second input portion into the plurality of input rings is performed based on a function of a distance of a given input ring from the gaze location in the input image, wherein thicknesses of the plurality of input rings increase on going from the gaze location towards a periphery of the input image according to said function, and wherein the method further comprises sending, to the display apparatus, information indicative of said function.

The present disclosure also relates to the display apparatus as described above. Various embodiments and variants disclosed above apply mutatis mutandis to the display apparatus.

Optionally, the display apparatus further comprises head-tracking means, wherein the processor of the display apparatus is configured to obtain, from the head-tracking means, the information indicative of the head pose of the user. Then, said information is sent to the encoder. Herein, the term "head-tracking means" refers to a specialized equipment for detecting and optionally, following changes in the head pose of the user, when the display apparatus in operation is worn by the user. The head-tracking means can employ at least one of: outside-in tracking, inside-out tracking, magnetic tracking. The head-tracking means could be implemented as at least one of: an optics-based positioning system (which utilizes, for example, infrared beacons and detectors, visible-light cameras and the like), an acoustics-based positioning system, a radio-based positioning system, a magnetism-based positioning system, an Inertial Measurement Unit (IMU). Such head-tracking means are well-known in the art.

Optionally, the display apparatus further comprises gaze-tracking means, wherein the processor of the display apparatus is configured to obtain, from the gaze-tracking means, the information indicative of the gaze direction of the user. Then, said information is sent to the encoder. Herein, the term "gaze-tracking means" refers to a specialized equipment for detecting and/or following gaze of the user, when the display apparatus in operation is worn by the user. The gaze-tracking means could be implemented as contact lenses with sensors, cameras monitoring a position of a pupil of the user's eye, and the like. Such gaze-tracking means are well-known in the art. It will be appreciated that gaze-tracking data (which constitutes the information indicative of the gaze direction) is collected repeatedly by the gaze-tracking means, as gaze of the user's eyes keeps changing whilst he/she uses the display apparatus. An up-to-date information indicative of the gaze direction allows for producing an up-to-date actively foveated XR environment for presenting at the display apparatus.

It will be appreciated that for each input image of a sequence of input images, the first encoded portion, the second encoded portion and the information indicative of relative positions of the first input portion and the second input portion are received. This facilitates in correctly assembling the decoded portions for each input image, in a manner that the first decoded portion corresponds to the gaze location of the user. Moreover, optionally, the second decoded portion surrounds the first decoded portion.

Optionally, the processor of the display apparatus is configured to decode the first encoded portion and the second encoded portion at a first decompression ratio and at least one second decompression ratio, respectively. During decoding, these encoded portions are decompressed (to different extents) to yield the decoded portions which are combined to generate a single output image. The first decompression ratio may or may not be equal to an inverse of the first compression ratio. Likewise, the at least one second decompression ratio may or may not be an inverse of the at least one second compression ratio.

Optionally, when the second input portion is divided into a plurality of input rings which are encoded at different compression ratios into the second encoded portion, the second encoded portion is decoded using a plurality of second decompression ratios to generate the second decoded portion. Optionally, the second decoded portion is generated by unpacking the plurality of rows of the second encoded portion.

It will be appreciated that the first decoded portion and the second decoded portion are assembled to have same relative positions with respect to each other as the relative positions of the first input portion and the second input portion.

Throughout the present disclosure, the term "output image" refers to an image that is obtained upon decoding the encoded portions of the input image. The output image comprises the first decoded portion and the second decoded portion. Optionally, the output image is an XR image. Optionally, in this regard, a sequence of output images constitutes the XR environment. The sequence of output images is displayed via the at least one light source. It will be appreciated that separate output images are displayed for each eye of the user.

Throughout the present disclosure, the term "light source" refers to an element from which light emanates. Optionally, a given light source is implemented as a display. In this regard, a given image is displayed at the given light source. Examples of the display include, but are not limited to, a Liquid Crystal Display (LCD), a Light-Emitting Diode (LED)-based display, an Organic LED (OLED)-based display, a micro OLED-based display, an Active Matrix OLED (AMOLED)-based display, and a Liquid Crystal on Silicon (LCoS)-based display. Optionally, a given light source is implemented as a projector. In this regard, a given image is projected onto a projection screen or directly onto a retina of the user's eyes. Examples of the projector include, but are not limited to, an LCD-based projector, an LED-based projector, an OLED-based projector, an LCoS-based projector, a Digital Light Processing (DLP)-based projector, and a laser projector.

Optionally, a given light source could be a multi-resolution light source, or a single-resolution light source. Multi-resolution light sources are configured to display images at two or more resolutions, whereas single-resolution light sources are configured to display images at a single resolution only. Optionally, the display apparatus comprises one light source per eye, wherein each light source is a multi-resolution light source. Alternatively, optionally, the display apparatus comprises at least two light sources per eye, the at least two light sources comprising at least one first light source and at least one second light source, wherein the at least one first light source is configured to display first images at a first resolution and the at least one second light source is configured to display second images at a second resolution, the second resolution being higher than the first resolution.

Optionally, the processor of the display apparatus is configured to send separate requests to the computing device or the rendering server for receiving separate input images corresponding to the first images and the second images. In such a case, the computing device or the rendering server generates the separate input images, which are separately encoded and sent to the display apparatus.

Optionally, the display apparatus further comprises at least one camera for capturing an image of a given real-world environment, wherein the processor of the display apparatus is configured to: obtain, from the at least one camera, the image of the real-world environment; and send, to the encoder, the image of the real-world environment. The at least one camera provides a video see-through arrangement for the display apparatus.

Optionally, in the display apparatus, the processor is configured to receive, from the encoder, information indicative of relative sizes of the first input portion and the second input portion, wherein, when decoding, the processor is configured to generate the first decoded portion and the second decoded portion based on the relative sizes of the first input portion and the second input portion.

As mentioned earlier, the size of the output image need not be the same as the size of the input image. In other words, a size of the first decoded portion and a size of the second decoded portion may or may not be different from the size of the first input portion and the size of the second input portion, respectively. However, the relative sizes of the first decoded portion and the second decoded portion are equal or nearly-equal to the relative sizes of the first input portion and the second input portion, thereby providing a consistent scale of the visual content in the input image and the output image.

Optionally, in the display apparatus, an angular width of the first decoded portion lies in a range of 5 degrees to 60 degrees.

Optionally, in the display apparatus, when decoding, the processor is configured to employ at least one first decoding algorithm and at least one second decoding algorithm to decode the first encoded portion and the second encoded portion, respectively.

DETAILED DESCRIPTION OF THE DRAWINGS

Referring to FIG. 1, illustrated is an architecture of an encoder 100 for encoding images, in accordance with an embodiment of the present disclosure. The to encoder 100 comprises a processor 102. The processor 102 is configured to implement a method of encoding images.

Figure 2:
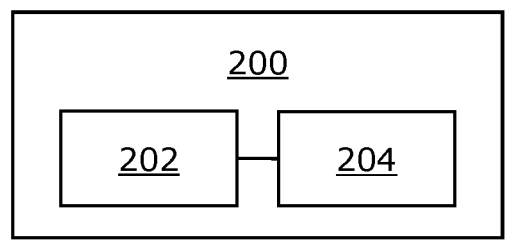
FIG. 2 illustrates a block diagram of an architecture of a display apparatus, in accordance with an embodiment of the present disclosure.

Referring to FIG. 2, illustrated is a block diagram of an architecture of a display apparatus 200, in accordance with an embodiment of the present disclosure. The display apparatus 200 comprises at least one light source (depicted as a light source 202) and a processor 204. The processor 204 is coupled to the light source 202.

FIGS. 1 and 2 are merely exemplary illustrations of the encoder 100 and the display apparatus 200, respectively, for sake of clarity only, and should not unduly limit the scope of the claims herein. A person skilled in the art will recognize many variations, alternatives, and modifications of embodiments of the present disclosure. For example, the display apparatus 200 may further comprise gaze-tracking means and/or head-tracking means.

Figure 3:
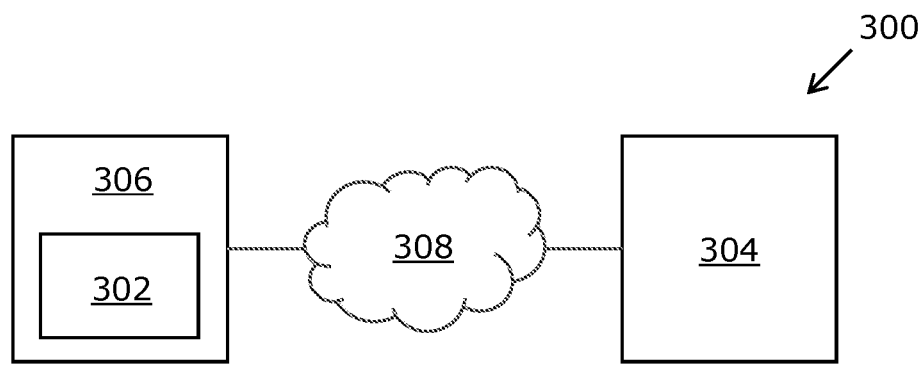
FIG. 3 illustrates an exemplary environment wherein an encoder and a display apparatus are used, in accordance with an embodiment of the present disclosure.

Referring to FIG. 3, illustrated is an exemplary environment 300 wherein an encoder 302 and a display apparatus 304 are used, in accordance with an embodiment of the present disclosure. The encoder 302 encodes input images to generate encoded portions of the input images, whereas the display apparatus 304 decodes the encoded portions to generate decoded portions which are assembled to generate output images. The encoder 302 is implemented in a computing device or a rendering server (depicted as element 306) that is communicably coupled to the display apparatus 304. The computing device or the rendering server 306 (and specifically, the encoder 302) is communicably coupled to the display apparatus 304 via a data communication network 308.

FIG. 3 is merely an exemplary illustration of the environment 300, for sake of clarity only, and should not unduly limit the scope of the claims herein. A person skilled in the art will recognize many variations, alternatives, and modifications of embodiments of the present disclosure. For example, the computing device or the rendering server 306 may be communicably coupled to the display apparatus 304 directly (i.e. without the data communication network 308).

Figure 4:
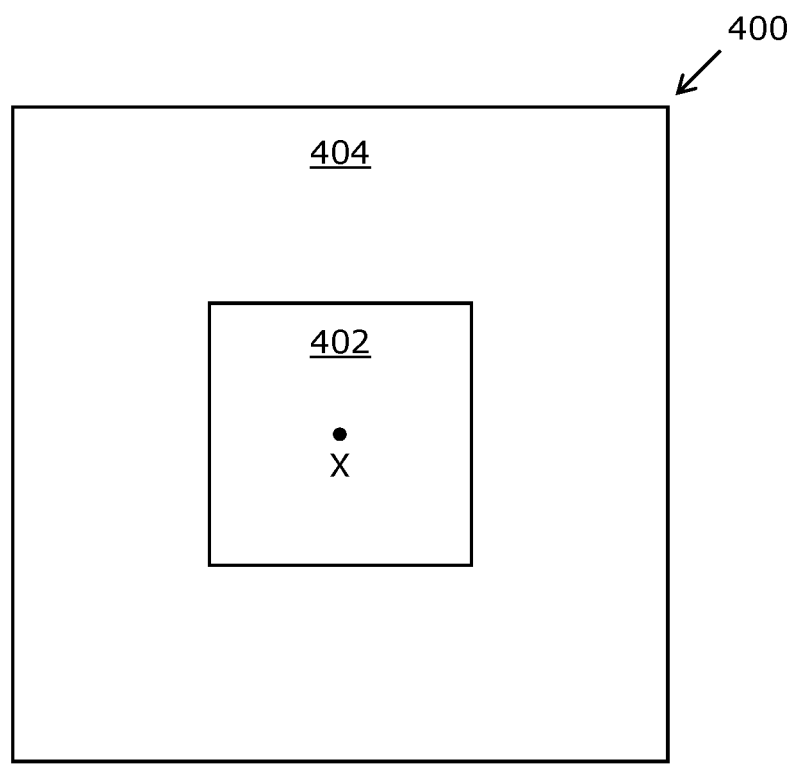
FIG. 4 illustrates how an input image is divided into a first input portion and a second input portion, in accordance with an embodiment of the present disclosure.

Referring to FIG. 4, illustrated is how an input image 400 is divided into a first input portion 402 and a second input portion 404, in accordance with an embodiment of the present disclosure. The first input portion 402 includes and surrounds a gaze location (depicted as point X) in the input image 400. The second input portion 404 surrounds the first input portion 402.

Figure 5:
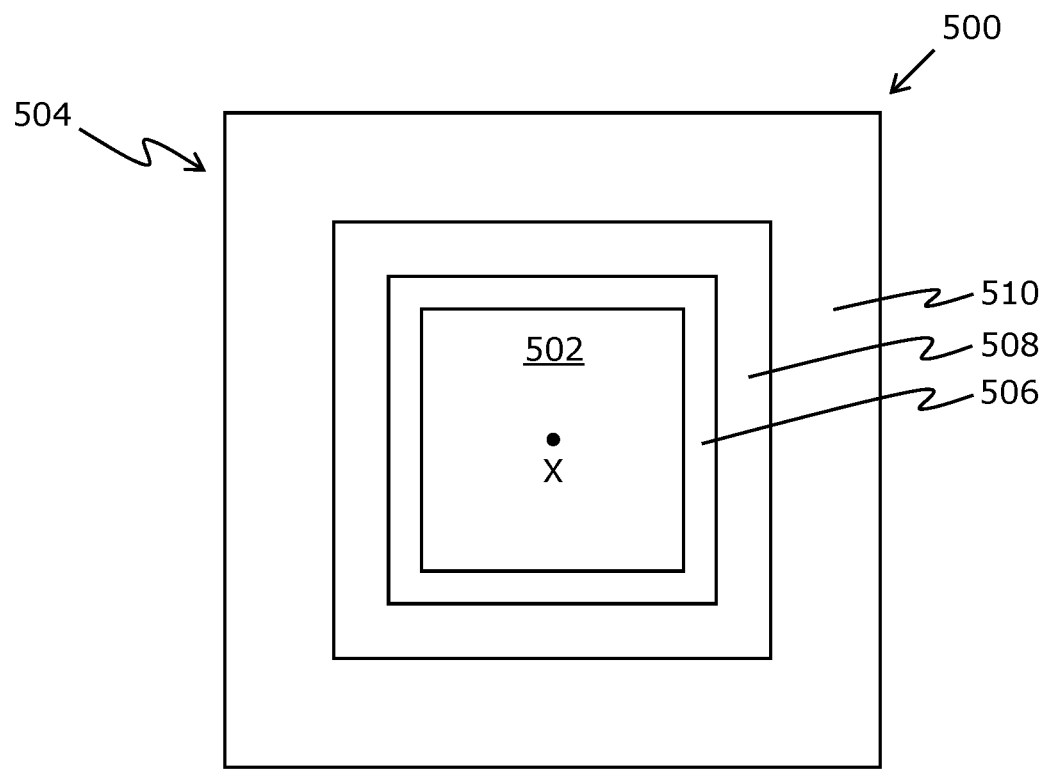
FIG. 5 illustrates how an input image is divided into a first input portion and a second input portion, in accordance with another embodiment of the present disclosure.

Referring to FIG. 5, illustrated is how an input image 500 is divided into a first input portion 502 and a second input portion 504, in accordance with another embodiment of the present disclosure. The first input portion 502 includes and surrounds a gaze location (depicted as point X) in the input image 500. The second input portion 504 surrounds the first input portion 502. Moreover, the second input portion 504 is divided into a plurality of input rings 506, 508, and 510 that are concentric with the first input portion 502. The first input portion 502 and the plurality of input rings 506, 508, and 510 are centered at the gaze location X in the input image 500. The first input portion 502 and the plurality of input rings 506, 508, and 510 are shaped as a simple closed curve. The input ring 506 is smaller than the input ring 508, and the input ring 508 is smaller than the input ring 510.

The division of the second input portion 504 into the plurality of input rings 506, 508, and 510 is based on a function of a distance of a given input ring from the gaze location X in the input image 500, wherein thicknesses of the plurality of input rings 506, 508, and 510 increase on going from the gaze location X towards a periphery of the input image 500 according to said function. As shown, thickness of the input ring 510 is greater than thickness of the input ring 508, which is greater than thickness of the input ring 506.

Figure 6:
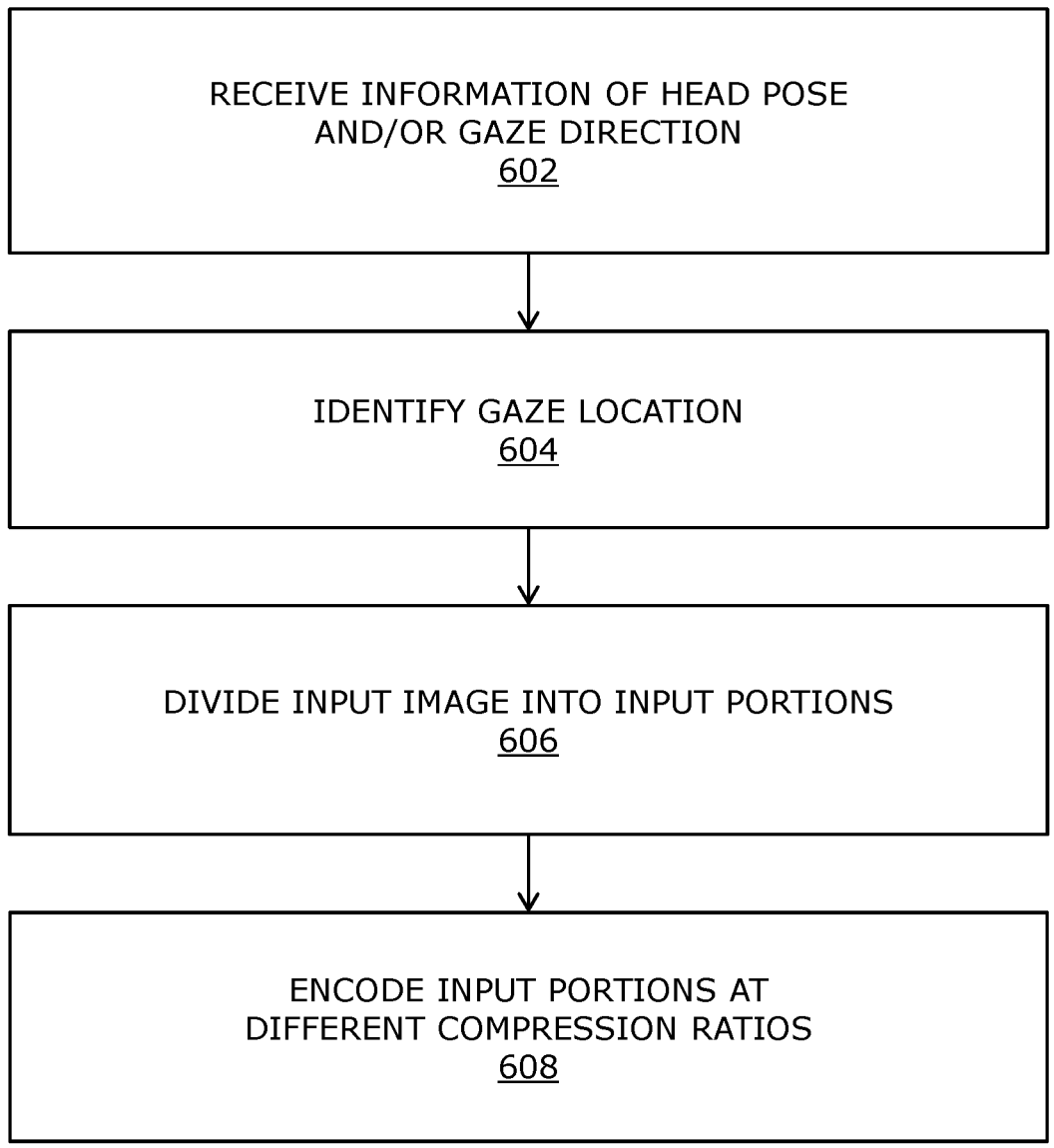
FIG. 6 illustrates steps of a method of encoding images, in accordance with an embodiment of the present disclosure.

FIG. 6 illustrates steps of a method of encoding images, in accordance with an embodiment of the present disclosure.

At step 602, information indicative of at least one of: a head pose of a user, a gaze direction of the user is received, from a display apparatus. At step 604, a gaze location in an input image is identified, based on the at least one of: the head pose of the user, the gaze direction of the user. At step 606, the input image is divided into a first input portion and a second input portion, wherein the first input portion includes and surrounds the gaze location. At step 608, the first input portion and the second input portion are encoded at a first compression ratio and at least one second compression ratio to generate a first encoded portion and a second encoded portion, respectively, wherein the at least one second compression ratio is larger than the first compression ratio.

The steps 602, 604, 606 and 608 are only illustrative and other alternatives can also be provided where one or more steps are added, one or more steps are removed, or one or more steps are provided in a different sequence without departing from the scope of the claims herein.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

What is claimed is:

1. A method for encoding images, the method comprising:
   receiving, from a display apparatus, information indicative of at least one of a head pose of a user and a gaze direction of the user;
   identifying a gaze location in an input image, based on the at least one of the head pose of the user and the gaze direction of the user;
   dividing the input image into a first input portion and a second input portion, wherein the first input portion includes and surrounds the gaze location;
   dividing the second input portion into a plurality of input rings that are concentric with the first input portion; and
   encoding the first input portion and the second input portion at a first compression ratio and at least one second compression ratio to generate a first encoded portion and a second encoded portion, respectively, wherein the at least one second compression ratio is larger than the first compression ratio, and wherein the second input portion is encoded by packing the plurality of input rings into the second encoded portion, the second encoded portion having a plurality of rows, a given input ring being packed into a corresponding row of the second encoded portion.

2. The method of claim 1, further comprising sending, to the display apparatus, the first encoded portion, the second encoded portion, information indicative of relative positions of the first input portion and the second input portion, and optionally, information indicative of relative sizes of the first input portion and the second input portion.

3. The method of claim 1, wherein an angular width of the first input portion lies in a range of 5 degrees to 60 degrees.

4. The method of claim, 1, wherein the first compression ratio is smaller than a predefined number, and the at least one second compression ratio is larger than the predefined number.

5. The method of claim 1, wherein the at least one second compression ratio is larger than twice the first compression ratio.

6. The method of claim 1, wherein the first input portion and the second input portion are encoded by employing at least one first encoding algorithm and at least one second encoding algorithm, respectively.

7. The method of claim 1, wherein the first input portion and the plurality of input rings are shaped as a simple closed curve, wherein the first input portion and the plurality of input rings are centered at the gaze location in the input image, and
wherein the step of encoding comprises encoding the plurality of input rings at different compression ratios into the second encoded portion, wherein a compression ratio employed to encode a given input ring is smaller than a compression ratio employed to encode another input ring that is larger than the given input ring.

8. The method of claim 7, wherein the step of dividing the second input portion into the plurality of input rings is performed based on a function of a distance of a given input ring from the gaze location in the input image, wherein thicknesses of the plurality of input rings increase on going from the gaze location towards a periphery of the input image according to said function, and wherein the method further comprises sending, to the display apparatus, information indicative of said function.

9. An encoder for encoding images, the encoder comprising a processor configured to:
receive, from a display apparatus, information indicative of at least one of a head pose of a user and a gaze direction of the user;
identify a gaze location in an input image, based on the at least one of the head pose of the user and the gaze direction of the user;
divide the input image into a first input portion and a second input portion, wherein the first input portion includes and surrounds the gaze location;
divide the second input portion into a plurality of input rings that are concentric with the first input portion; and
encode the first input portion and the second input portion at a first compression ratio and at least one second compression ratio to generate a first encoded portion and a second encoded portion, respectively, wherein the at least one second compression ratio is larger than the first compression ratio, and wherein the second input portion is further encoded by packing the plurality of input rings into the second encoded portion, the second encoded portion having a plurality of rows, a given input ring being packed into a corresponding row of the second encoded portion.

10. The encoder of claim 9, wherein the processor is configured to send, to the display apparatus, the first encoded portion, the second encoded portion, information indicative of relative positions of the first input portion and the second input portion, and optionally, information indicative of relative sizes of the first input portion and the second input portion.

11. The encoder of claim 9, wherein an angular width of the first input portion lies in a range of 5 degrees to 60 degrees.

12. The encoder of claim 9, wherein the first compression ratio is smaller than a predefined number, and the at least one second compression ratio is larger than the predefined number.

13. The encoder of claim 9, wherein the at least one second compression ratio is larger than twice the first compression ratio.

14. The encoder of claim 9, wherein, when encoding, the processor is configured to employ at least one first encoding algorithm and at least one second encoding algorithm to encode the first input portion and the second input portion, respectively.

15. The encoder of claim 9, wherein the first input portion and the plurality of input rings are shaped as a simple closed curve, wherein the first input portion and the plurality of input rings are centered at the gaze location in the input image, and
wherein, when encoding, the processor is configured to encode the plurality of input rings at different compression ratios into the second encoded portion, wherein a compression ratio employed to encode a given input ring is smaller than a compression ratio employed to encode another input ring that is larger than the given input ring.

16. The encoder of claim 15, wherein the processor is configured to:
divide the second input portion into the plurality of input rings based on a function of a distance of a given input ring from the gaze location in the input image, wherein thicknesses of the plurality of input rings increase on going from the gaze location towards a periphery of the input image according to said function; and
send, to the display apparatus, information indicative of said function.

17. A display apparatus comprising at least one light source and a processor configured to:
send, to an encoder, information indicative of at least one of a head pose of a user and a gaze direction of the user;
receive, from the encoder, a first encoded portion, a second encoded portion and information indicative of relative positions of a first input portion and a second input portion of an input image, the input image being divided at the encoder into the first input portion and the second input portion based on the at least one of the head pose of the user and the gaze direction of the user, the second input portion being divided into a plurality of input rings that are concentric with the first input portion, the first encoded portion and the second encoded portion being generated at the encoder by encoding the first input portion and the second input portion at a first compression ratio and at least one second compression ratio, respectively, the at least one second compression ratio being larger than the first compression ratio, and the second input portion being further encoded by packing the plurality of input rings into the second encoded portion, the second encoded portion having a plurality of rows, a given input ring being packed into a corresponding row of the second encoded portion;
decode the first encoded portion and the second encoded portion to generate a first decoded portion and a second decoded portion, respectively;
assemble the first decoded portion and the second decoded portion, based on the relative positions of the first input portion and the second input portion, to generate an output image; and
display the output image via the at least one light source.

18. The display apparatus of claim 17, wherein the processor is configured to receive, from the encoder, information indicative of relative sizes of the first input portion and the second input portion, and
wherein, when decoding, the processor is configured to generate the first decoded portion and the second decoded portion based on the relative sizes of the first input portion and the second input portion.

19. The display apparatus of claim 17, wherein an angular width of the first decoded portion lies in a range of 5 degrees to 60 degrees.

20. The display apparatus of claim 17, wherein, when decoding, the processor is configured to employ at least one first decoding algorithm and at least one second decoding algorithm to decode the first encoded portion and the second encoded portion, respectively.

* * * * *